United States Patent [19]

Brouard et al.

[11] Patent Number: 5,098,604
[45] Date of Patent: Mar. 24, 1992

[54] CATION-ACTIVE COMPOSITIONS AND THEIR APPLICATION TO BITUMINOUS EMULSIONS

[75] Inventors: Rene L. A. Brouard, L'Isle-Adam; Luc E. A. Navascues, Paris, both of France

[73] Assignee: Ceca, S.A., France

[21] Appl. No.: 455,433

[22] PCT Filed: Mar. 28, 1989

[86] PCT No.: PCT/FR89/00144

§ 371 Date: Nov. 16, 1989

§ 102(e) Date: Nov. 16, 1989

[87] PCT Pub. No.: WO89/09089

PCT Pub. Date: Oct. 5, 1989

[30] Foreign Application Priority Data

Mar. 30, 1988 [FR] France .................. 88 04166

[51] Int. Cl.$^5$ ............ B01F 17/16; B01F 17/46; B01J 13/00
[52] U.S. Cl. ................ 252/311.5; 106/277; 252/314; 252/357
[58] Field of Search ............ 252/311.5, 357; 106/277

[56] References Cited

U.S. PATENT DOCUMENTS

| | | | |
|---|---|---|---|
| 2,886,458 | 5/1959 | Ceintrey | 252/311.5 X |
| 2,930,761 | 3/1960 | Charret | 252/357 X |
| 3,170,938 | 2/1965 | Levis, Jr. | 252/357 X |
| 3,518,101 | 6/1970 | Gzemski et al. | 252/311.5 X |
| 3,928,061 | 12/1975 | Hellsten et al. | 106/277 X |
| 3,975,295 | 8/1976 | Koch | 252/357 |
| 3,999,942 | 12/1975 | Heid et al. | 8/568 |
| 4,313,895 | 2/1982 | Richmond et al. | 106/273 N X |

FOREIGN PATENT DOCUMENTS

| | | |
|---|---|---|
| 0051030 | 5/1982 | European Pat. Off. |
| 0111983 | 6/1984 | European Pat. Off. |
| 1266909 | 6/1961 | France |
| 1462981 | 12/1966 | France |

Primary Examiner—Richard D. Lovering
Attorney, Agent, or Firm—Sigalos & Levine

[57] ABSTRACT

New cation-active amine compositions, liquid at ambient temperature, which do not form concretions by prolonged maintenance at temperatures in the region of 0° C., nor by exposure to the open air, and which do not contain solvents, comprising from 20 to 80% branched-chain alkyletheramines and 80 to 20% oxyalkylated alkylpolyamines. Application of their acid liquid solutions as emulsifying phases of road bitumen, and improved manufacturing process for road bitumen emulsions.

10 Claims, No Drawings

CATION-ACTIVE COMPOSITIONS AND THEIR APPLICATION TO BITUMINOUS EMULSIONS

BACKGROUND OF THE INVENTION

1. Technical Field

The present invention pertains to liquid compositions of fatty amines and similar products, with cation-active properties.

The amines, represented by the general formula R—$NH_2$ in which R is a hydrocarbon radical having at least ten carbon atoms, develop not only the ordinary chemical properties that characterize the amine class, and notably a basic force comparable to that of ammonia, but also surface-active properties, notably to water/liquid hydrocarbon interfaces and very pronounced adsorption properties on mineral surfaces. Industry employs these properties on a large scale, for example, for forming aqueous emulsion of various liquids, in particular the black binders for road construction, the enrichment of ores by ore flotation, and in a general manner for the most diverse treatment of mineral surfaces such as, for example, development of an antistatic effect on polymers of fibers, dewetting of metal surfaces and reduction of their corrosion, dispersion of pigments in oils, hydrophobation of sols, reduction of the agglomeration capacity of fertilizer grains, and the like. (See Cationic Surfactants by Eric Jungermann, M. Dekker publisher, 1970).

In fact, these properties which for linguistic convenience we will subsequently refer to herein as "cation-active properties", are found to be developed at the highest level in compounds that include at least one aminated nitrogen and at least one hydrophobic group including a hydrocarbon chain with at least ten carbon atoms. These formulas correspond to a broader formula than the standard formula of fatty amines in the strict sense, and which can be represented by R—Z—$NH_2$, in which Z is a divalent polar group. By listing several examples for the Z group, the person skilled in the art will immediately recognize very common products. With Z=aminopropyl, there are the alkylaminopropylamines, such as tallow-N-propylenediamine which is widely known in the road-building industry; with Z=oxypropyl, there are the alkyloxypropylamines, referred to as ether amines, used in flotation; with Z=amidoethyl, there are the amidoamines and their cyclization products the imidazolines, largely employed as adhesivity doping agents for paving roads and the like.

2. Prior Technology

However, because of the existence of a long chain required for the development of these particular properties, these products have a relatively high melting point, and the corresponding industrial products generally have a pasty consistency at room temperature. This is an annoying characteristic from various points of view.

In the first place, transfers of these products in this form are limited to manual manipulations, which are not free from danger. They are, in fact, very aggravating for the skin and mucosa and not free from general toxicity.

Melting of these products occurs at relatively low temperatures, and the melted forms at 40°-60° C. are definitely very fluid, and thus can be pumped and dosed with precision equipment, avoiding all bodily contact. But, at these temperatures, they frequently emit caustic volatile products (ammonia, methylamine, propylamine, etc.), originating either from the industrial impurities which are almost obligatory in this type of compounds, or from the degradation products arising from their heating and their storage even for short periods at the temperatures that they need to reach in order to be sufficiently liquid. It is necessary to add that this melting at relatively low temperatures is difficult to carry out in industrial practice without the risk of overheating, and that in any case, such melting operations are extremely lengthy because of the well-known poor thermal exchange capacity of the fatty compounds.

Fluid compositions have been realized at room temperature by employing solvents. Leaving aside the effect of loss of efficacy related to dilution, other disadvantages of the use of solvents are well known, such as the heavy solvents are found, useless or undesirable, in the final products and the light solvents can certainly be eliminated but are also sources of flammability and/or pollution. In addition, formulations of long-chain cation-active compounds in solvents generally do not exhibit satisfactory behavior when stored at low temperatures, as will be shown below.

The chemist will know how to implement certain modifications of these molecules in order to reduce their melting points. This is what was done by oxyalkylation of alkylamines and alkylpropylenediamines, as is described for example in U.S. Pat. No. 2,930,701, in which concentrated compositions for shampoos were realized using totally oxyethylated chlorhydric solutions of oleylpropylenediamines. But it is also known that oxyalkylation results in the sacrifice of part of the cation-active properties. This has been more-or-less resolved by judicious selection of the nature of the oxyalkylene substituent and of the molar ratio of oxyalkylation (see, for example, French Patent No. 1,462,981, which discloses alkylpropylenediamines oxyethylated on the internal nitrogen, French Patent No. 1,266,909, which divulges oxyethylated tallow-or soya-propylenediamines, or French Patent Appln. No. 80,22932, which divulges compositions based on oxypropylated tallow-propylenediamines). In truth, these modification, even effected carefully, can result in an acceptable liquidity at room temperature, but this liquidity is not maintained during storage at negative temperatures. These products can be stored in barrels in the open air or under non-climate-controlled shelters. Concretions then appear, which persist for a long time after restoration of milder temperatures. The result is a segregation of the products with noteworthy differences in composition between the melted products and the concretions. These undesired phenomena also occur with the formulations in solvent that were discussed above, and also with formulations resulting from the combination of an amine in liquid form with a pasty or solid amine, such as the compositions disclosed in U.S. Pat. No. 3,975,295, of tallow-diamines with alkylamines oxyethylated in the presence of absence of alcohol solvents.

More recently (see French Patent Appl. No. 80,07091), success has been achieved in greatly reducing the melting point of N-tallow-propylenediamines without perceptibly changing their cation-active behavior by methylation of the secondary nitrogen, but these N-alkyl-N-methylpropylenediamines exhibit a negative ability to very quickly absorb the carbon dioxide and water from the atmosphere by yielding abundant concretions, such that these products lose their liquidity by simple exposure or handling in open air.

Presentation of the Invention

The purpose of the present invention is to remedy these shortcomings. Its objective is to provide compositions of non-flammable, aminated cation-active derivatives which are absolutely liquid at room temperature, which retain their liquidity when stored indefinitely exposed to the atmosphere, which do not lead to the formation of gels, precipitates or deposits when they are maintained for extended periods at temperatures close to zero degrees centigrade or which do not lead to the formation of such gels, precipitates or deposits which persist for a long time after return to room temperature.

The inventors found that it was possible to realize such compositions by combining with fatty amines, diamines or polyamines partially substituted at the nitrogen by an alkylene oxide such as ethylene oxide, propylene oxide, butylene oxide (which for convenience of the presentation, shall be referred to below simply as oxyalkylated amines); alkyletheramines of the general formula $$R-O-(CH_2)_n-[NH-(CH_2)_m-]_p-NH_2$$

in which
n is a whole number equal to 2 or 3,
m is a whole number equal to 2 or 3,
p is a number which can have any value from 0 to 3, and
R is a branched alkyl chain, of the type $$CH_3-[-CH-CH-]_q-CH_2$$
$$\phantom{CH_3-[-}|$$
$$\phantom{CH_3-[-}CH_3$$

with q ranging from 2 to 5.

Since industrial products are frequently homologous mixtures, their centesimal formula can be interpreted by values of q which are not whole numbers. (In the text that follows and for convenience of the presentation, the term "etheramines" will be understood to refer to alkyletheramines as defined above).

In the compositions in accordance with the invention, the weight ratio between the oxyalkylated amines and the etheramines is between about 20/80 and 80/20. Such compositions in accordance with the invention are obtained without great difficulty by simple mixture at room temperature of compounds of the oxyalkylated amine type and compounds of the etheramine type, the operation being quite easy because these substances are liquid at room temperature or at least are easily meltable at temperatures not exceeding 50° C., and that in liquid state, they are soluble in each other at any proportion.

Among these etheramines as defined by the invention, one prefers the alkyloxypropyl-N-propylenediamines, which are compounds responding to the general formula:

$$R-O-CH_2-CH_2-CH_2-NH-CH_2-CH_2-CH_2-NH_2$$

The most common procedure for obtaining these compounds consists of condensing an alcohol with acrylic nitrile, hydrogenating the ether-nitrile formed in ethermonoamine, then condensing again this product with acrylic nitrile and hydrogenating the etheraminonitrile in etherdiamine. This mode of preparation is derived simply from the mode disclosed by American Cyanamid Co. in the "The Chemistry of Acrylonitrile", (NY, 1956, p. 216). In order to obtain the etheramines in accordance with the invention, one employs branched-chain alcohols, which are industrially available by hydroformylation of oligopolypropylenes, in particular of tetrapropene (see Chimie Organique Industrielle, K. Weissermel and H. J. Arpe, Masson publisher, 1981, p. 191). The preferred compounds of the oxyalkylated amine type in accordance with the invention are selected from the family of the oxyalkylated alkylpropylene diamines.

They can be represented by the general formula:

$$R'-NQ_1-CH_2-CH_2-CH_2-NQ_2Q_3$$

in which $Q_1$, $Q_2$ and $Q_3$ are each hydrogen or a hydroxyethyl group $CH_2-CH_2-OH$, or a hydroxyethyloxyethyl group $CH_2-CH_2-O-CH_2-CH_2-OH$, and can be identical or different, with the sole condition being that they are not all hydrogens.

They are obtained in the very classical manner by reaction of the ethylene oxide on the corresponding alkylpropylenediamines. In accordance with the invention, one employs derivatives with a linear, saturated or unsaturated, alkyl chain R', including 10 to 22 carbon atoms. In practice, one start with diamines constituted of industrial mixtures of compounds with chains that have about 18 carbon atoms and which contain a noteworthy proportion of mono-unsaturated chains; they are commonly referred to as oleic compounds.

Possibilities of Industrial Application

The invention also has a purpose of the application of these cation-active compounds, notably for the manufacture of bituminous emulsions based on aminated emulsifier. The use of the compounds in accordance with the invention give to this manufacture a novel and original character, in that the emulsifiers can be be prepared, stored and employed at room temperature. It makes it possible to resolve various particularly annoying problems in this industry, notably those of the automation of installations that require liquid phases, those of the physical or chemical alteration of emulsifiers, as such or formulated, during their storage or handling. The use at room temperature of aqueous phases based on the compositions in accordance with the invention also make it possible to successfully put hard bitumens into emulsion in industrial installations operating at atmospheric pressure, because of the reduction in the supply of heat by the aqueous phase.

EXAMPLES

The following examples, which are not limiting, will make possible the better comprehension of the invention and will demonstrate its multiple advantages.

The compounds in the examples are represented by symbols which are explained in the following table. The products in the examples are either products resulting from laboratory manufacture or are products on the market. In the latter case, the commercial names of the products employed have been specified.

| Symbol | Product |
|---|---|
| SPDA | Tallow-propylenediamine (the industrial product used in the experiment is Dinoram S, from CECA S.A.) |

-continued

| Symbol | Product |
|---|---|
| OPDA | Oleylpropylenediamine (the industrial product used in the experiment is Dinoram O, from CECA S.A.) |
| OPDA - 1.5 OE, OPDA - 2.0 OE, OPDA - 2.5 OE | Oleylpropylenediamine oxyethylated, respectively, at 1.5, 2.0 and 2.5 moles of ethylene oxide (For OPDA 2.0 OE, Dinoramox 0/2OE from CECA S.A. was used) |
| SPDA - 1.5 OP | Tallow-propylenediamine oxypropylated at 2 moles of propylene oxide (Dinoram SL from CECA S.A. was used) |
| OPDAM | N-oleyl, N-methyl, propylene diamine |
| SPDAM | N-tallow, N-methyl, propylene diamine |
| $nC_{13}$ OPPDA | N-tridecyloxypropyl-propylenediamine (A mixture of tridecyl and pentadecyloxypropyl propylene diamine, Kenogard $C_{13}$ and $C_{15}$ was used.) |
| $iC_{13}$ OPPDA | Isotridecyloxypropyl-propylene diamine |
| N-ALKIZ | Alkyl-imidazoline-amine (Emulsamine L60 from CECA was used.) |

EXAMPLE 1

A comparison will be made here of the physical performance of the various compounds and products in accordance with the invention after exposure to low temperatures. On the one hand, a freezing/defreezing test was carried out, during which the product in a test-tube is subjected to intense cooling by being plunged in an acetone/dry ice cold bath. The temperature decline within the product is monitored and the temperature, Tf, at which it solidifies is recorded. The tube is then removed from the cold bath and the product is allowed to spontaneously heat up in the environment. The temperature, Tdf, at which the beginning of melting is observed, is recorded. On the other hand, we observed the appearance of the product stored under normal conditions at laboratory temperature, after exposure for 12 hours at 0° C. and after extended exposure for seven days at this 0° C. temperature. The following table presents the performance of several representative cation-active compositions.

| Product | % | Freezing test Tf | Tdf | Normal | Appearance 12 hr at 0° C. | 7 days at 0° C. |
|---|---|---|---|---|---|---|
| OPDA | 100 | +7 | +14 | Precipitated | Precipitated | Precipitated |
| $iC_{13}$.OPPDA | 100 | −28 | −20 | Fluid | Fluid | Fluid |
| OPDA | 50 | −8 | −2 | Precipitated | Precipitated | Precipitated |
| $iC_{13}$.OPPDA | 50 | | | | | |
| OPDA-1,5.OE | 100 | −12 | −6 | Fluid | Fluid | Viscous |
| OPDA-1,5OE | 50 | −21 | −16 | Fluid | Fluid | Fluid |
| $iC_{13}$.OPPDA | 50 | | | | | |
| OPDA-2.OE | 100 | −13 | −7 | Fluid | Fluid | Viscous |
| OPDA-2.OE | 50 | −21 | −16 | Fluid | Fluid | Fluid |
| $iC_{13}$.OPPDA | 50 | | | | | |
| OPDA-2.5.OE | 100 | −11 | −4 | Fluid | Fluid | Fluid |
| OPDA-2.5.OE | 50 | −19 | −13 | Fluid | Fluid | Fluid |
| $iC_{13}$.OPPDA | 50 | | | | | |
| SPDA-2 OP | 100 | +4 | +8 | Fluid | Solid | Solid |
| SPDA-2 OP | 50 | −12 | −7 | Liquid | Liquid | Liquid |
| $iC_{13}$.OPPDA | 50 | | | | | |

The table shows that only etheramine and the compositions based on etheramine and oxyalkylated amines are liquid at room temperature and apparently liquid at temperatures below 0° C. and also preserve in an unexpected manner their fluidity after prolonged exposure to this temperature of 0° C.

EXAMPLE 2

Performance of the Products upon Exposure to the Atmosphere

Here we observed the formation of crusty compounds upon exposure to the air. These compounds are essentially due to the formation of carbamates and also hydrates by reaction with the carbon dioxide and moisture from the atmosphere. The composition of these substances has been poorly determined and they are both solids and insoluble in the amine from which they originate.

In the following table, descriptions are presented of several cation-active compositions after 24-hour exposure to open air.

| Product | Appearance |
|---|---|
| OPDA2.OE | Unchanged |
| SPDA 2.OP | Unchanged |
| OPDA 2.O3 50% $iC_{13}$ OPPDA, 50% | Unchanged |
| SPDA 2.OP 50% $iC_{13}$ OPPDA 50% | Unchanged |
| SPDA 1.5 OP | Unchanged |
| N-ALKIZ | Very turbid and precipitated liquid |
| OPDAM | Surface crust |
| SPDA | Very thick surface crust and precipitated |
| $C_{13}$ OPPDA | Surface crust and precipitated |
| SPDAM 50% $iC_{13}$ OPPDA 50% | Surface crust |

We can see here that resistance to deterioration in the atmosphere is the property of the oxyalkylated amines and the branched-chain etheramines, and that the compositions containing noteworthy proportions of unstable cation-active products remain unstable in the atmosphere.

EXAMPLE 3

Homogeneity of Aqueous Formulation of Cation-Active Aminated Compounds

The industrial use of cation-active amines generally requires that they be in aqueous solution. Since these compounds are insoluble in water, use is made of amine salt solutions, very generally the chlorhydrates, which themselves only have a very limited solubility.

In the present example, as is often the case in industry, cationic emulsions of bitumen were prepared, with solutions containing 5 kilograms of aminated derivative per m$^3$ of solution, by starting with the dispersement of the cation-active composition in water brought in advance to ca. 60° C., then adding commercial hydrochloric acid in an amount sufficient to set the pH value at 2, then allowing the solution to cool at room temperature. The solutions were examined after being allowed to rest for 24 hours.

It was found that the alkyldiamines of the SPDA or OPDA type always yield, after cooling, shimmering solutions that allow deposition of a portion of their active material in the form of insoluble chlorhydrates; that SPDA-2.0P yields turbid solutions with slight deposit. In contrast, the solutions prepared using the compositions in accordance with the invention as well as their individual components, i.e., the oxyalkylated amines and the etheramines as defined above in the context of the invention, always remain clear and thus absolutely homogeneous.

EXAMPLE 4

As was shown in the preceding example, industrial practice involves dispersing the aminated derivative in hot water prior to neutralizing it with an acid.

Certain of these aminated derivatives exhibit a serious defect under these conditions, which result from hot hydration phenomena and which are manifested by the formation of gummy products, which will not disperse in hot water, and which as a result only dissolve very slowly upon addition of acid. This very annoying performance can be demonstrated by a very simple test which consists of adding 5 g of the aminated derivative to 50 mL of water at 60° C. in a one-liter beaker under slow stirring, and watching the evolution of the system. The test showed:

(i) that SPDA dissolves by yielding an unstable emulsion which, as soon as the stirring is stopped, is transformed into oily droplets which rise to float on the surface, (ii) that OPDA forms an unstable emulsion, within which quickly collect lumps with a rubbery appearance, which cannot be dispersed even under intense agitation; and (iii) that a composition in accordance with the invention, such as the composition comprised of 60% OPDA 1.5.OE and 40% iC$_{13}$OPPDA, yields a stable emulsion which does not perceptibly change when the operation is continued.

EXAMPLE 5

Cold preparation of chlorhydrate solutions of alkylaminated substances as dispersant phase for the preparation of emulsions for paving bitumens. In this example, we present the results obtained with the preparation of solutions of cation-active compositions at the concentration of 5 Kg of active compound per ton or m$^3$ of solution. Such solutions are commonly employed as dispersant phases for the preparation of paving bitumen emulsions. But, rather than carrying out the procedure of 60° C., as is conventional in this industry, the procedure was implemented without any heating. Under slow stirring, the cation-active compound is dispersed directly in room temperature water, then commercial hydrochloric acid is added slowly in the appropriate amount such that the pH value is at 2.

The operation was impossible with SPDA; the diamine did not disperse and the subsequent introduction of hydrochloric acid was not immediately followed by any improvement in the heterogeneity of the mixture.

SPDA 2.OP yielded an acceptable dispersion of the aminated composition in the form of an emulsion. After addition of commercial hydrochloric acid (d=1.18), in the amount of 7.5 liters per m$^3$ of dispersion, the pH value was set at 2 and one obtained an aqueous phase apparently free of solid or semi-solid particles, but which nevertheless was very cloudy.

The dispersion of N-ALKIZ in cold water was difficult and incomplete. The appearance of the mass improved slowly after addition of 11.25 liters of hydrochloric acid per m$^3$ and one obtained almost instantaneously an absolutely clear aqueous phase.

With a composition in accordance with the invention, comprised of 50% OPDA 2.OE and 50% iC$_{13}$OPPDA, the dispersion in cold water is immediate and, after addition of 7.5 liters commercial hydrochloric acid per m$^3$, one obtains practically instantly an absolutely clear aqueous phase.

This novel and unexpected possibility to obtain from the compositions in accordance with the invention cation-active solutions ready to be used for dispersion and salification operations conducted under cold conditions and within a very short period of time constitutes a large industrial advantage.

EXAMPLE 6

Concentrated aqueous solutions. There are various incontestable advantages in the preparation of aqueous solutions of cation-active aminated derivatives which are as concentrated as possible, which are and remain homogeneous, and moreover, which do not exhibit any signs of gelling, and are therefore instantaneously pumpable and instantaneously dissolvable under cold conditions.

It will be shown here that it is possible to realize such concentrated solutions with the cation-active compositions in accordance with this invention. The goal was to prepare a solution which contained 125 kg per m$^3$ of solution of the composition formed from 60% OPDA 2.OE and 40% is iC$_{13}$OPPDA. For this purpose, 50 g of the above cation-active solution was placed in a beaker, then 400 mL of 50° C. water was poured in. Under slow stirring, a homogeneous dispersion was obtained almost instantly. One then added 21.5 mL of commercial hydrochloric acid (d=1.18) and a clear solution with a pH value of 2 was obtained immediately.

The same operation was repeated with water at room temperature and the result was identical.

The solutions thereby obtained can be stored indefinitely.

They can be diluted, for example, with 24 volumes of water acidified to the same pH value of 2. One thereby very easily obtains from a stock solution, a solution containing 0.5% of cation-active compounds which has the same appearance as the solution of similar composition in Example 5 obtained by the direct route.

As a comparison, if one prepared solutions at the same concentration of 12.5% with SPDAM, the solution prepared in the hot state is clear when it is returned to room temperature. It still remains clear 24 hours after its preparation, but a deposit forms after 48 hours. The solution prepared in the cold state encounters some difficulties due to a beginning of gelling, which disappears as soon as the acid is added. However, one thereby ended up with a cloudy solution, which deposited in less than 24 hours.

EXAMPLE 7

The products in accordance with the invention can be used for fabrication of paving bitumen emulsions. The example relates to conventional emulsions for surface coatings, containing 60% of bitumen, and which are obtained following a procedure which is well known by a person skilled in the art, and which consists of admixing together in a turbo-mixer the bitumen at a temperature on the order of 140° C. and a dispersant phase constituted of a hydrochloric solution of an appropriately selected emulsifier.

The following characteristics of the emulsion obtained are of interest:

(i) pH value;

(ii) viscosity (in $mm^2/s$, measured according to the standard AFNOR T 66-020);

(iii) retention on a 0.630 mm secreen, expressed in per mil in relation to the emulsions (according to the Laboratoire Central des Ponts et Chausés [Central Laboratory of Bridges and Roads] standard RLE-AC.2.1965);

(iv) mean diameter of the bitumen particles in micrometers (measured with a laser granulometer, SILAS device, model 715);

(v) the 7-day storability (measured by the difference in the bitumen content by percent between two samples taken from the surface and the bottom of the storage container, respectively, according to the standard AFNOR T 66-022);

(vi) the breaking index (according to the standard AFNOR T 66-017); and (vii) the adhesivity on siliceous gravel (according to the standard AFNOR T 66-018).

As references, use was made of bitumen emulsions of 188/220 penetration, prepared using an aqueous phase of SPDA neutralized to a pH value of 2 with hydrochloric acid, and containing 600 kg of bitumen and respectively, 1.5 and 2 kg of SPDA per ton of emulsions. These emulsions are very common fabricated products. The laboratory preparations had the following characteristics:

| Emulsifier | SPDA | SPDA |
|---|---|---|
| Kg/ton of emulsion | 1.5 | 2 |
| pH value of the emulsion | 2 | 2 |
| Sieving at 0.60 mm retained % | 0 | 0 |
| Viscosity ($mm^2s$) | 34 | 25 |
| Storability at 7 days % | 12 | 10 |
| Mean diameter ($\mu m$) | 5.6 | 2.6 |
| Breaking index | 158 | 164 |
| Adhesivity | 100 | 100 |

The emulsions prepared with compositions such as with $C_1 = 60\%$ OPDA 2.OE + 40% $iC_{13}$ OPPDA and $C_2 = 50\%$ OPDA 2.OE + 50% $iC_{13}$ OPPDA, show both that it is possible to prepare, using compositions in accordance with the inventions, correct bituminous emulsions for repaving and that the cation-active properties of such compositions compare excellently with those of the traditional alkylpropylene diamines.

The characteristics of these emulsions are shown in the table below.

| Emulsifier | $C_1$ | $C_2$ |
|---|---|---|
| Kg/ton of emulsion | 1.5 | 1.5 |
| pH value of the emulsion | 2 | 2 |
| Sieving at 0.60 mm retained % | 0.15 | 0.05 |
| Viscosity ($mm^2s$) | 46 | 41 |
| Storability at 7 days % | 13 | 17 |
| Mean diameter ($\mu m$) | 6.6 | 5.8 |
| Breaking index | 132 | 139 |
| Adhesivity | 100 | 100 |

EXAMPLE 8

Procedures are carried out as in Example 7 for the comparison of emulsions prepared with SPDA and with composition $C_1$ accordance with the invention, with the difference, compared to the preceding example, that one uses aqueous phases that had been left at rest for 48 hours and that only the supernatant portion was taken. In this manner, we simulate an industrial fabrication based on aqueous phases prepared in advance and which would have aged by separation of insoluble salts from the emulsifier.

The results are present in the following table.

| Emulsifier | SPDA | $C_1$ |
|---|---|---|
| Kg/ton of emulsion | (1.5) | (1.5) |
| pH value of the emulsion | 2 | 2 |
| Sieving at 0.60 mm retained % | 2 | 0.06 |
| Viscosity ($mm^2s$) | 22 | 40 |
| Storability at 7 days % | 25 | 16 |
| Mean diameter ($\mu m$) | 14 | 6.1 |
| Breaking index | 80 | 135 |
| Adhesivity | 95 | 100 |

It can be seen that the emulsion obtained from the product in accordance with the invention is practically identical to that of Example 7. In contrast, the fabrication of the SPDA emulsion was greatly disturbed and the emulsion produced exhibited manifest signs of instability; high retention at 0.63 mm, strong settling in storage with traces of rupture, a high mean diameter, and a low rupture index, which are indications that the aqueous phase has become impoverished in active material due to sedimentation.

EXAMPLE 9

For comparative purposes, a hard bitumen emulsion with 40/50 penetration was prepared. The usual requirements for emulsifying this type of bitumen require that it be brought to a temperature of 160° C. Under these conditions, in order to be able to use the ordinary aqueous phases at the temperatures conventionally employed, i.e., circa 55° C., it is necessary to emulsify under a pressure of 2 bars, to avoid accidents in the colloidal mill itself, because of boiling of the emulsion being formed.

Preparation of the emulsion using equipment working at atmospheric pressure requires that the aqueous phase be at maximum at a temperature of 30° C. The attempt to do this with an aqueous phase prepared with SPDA failed completely. In contract, the emulsion prepared with the composition, $C_1$, in accordance with the invention yielded an emulsion with good characteristics, comparable to those obtained with SPDA under pressure. The results are present below.

| Emulsifier | SPDA | $C_1$ |
|---|---|---|
| Kg/ton of emulsion | 1.8 | 1.8 |
| pH value of the emulsion | 2.5 | 2.5 |
| Sieving at 0.60 mm retained % | 0 | 0 |
| Viscosity (mm²s) | 27 | 29 |
| Storability at 7 days % | 10 | 13 |
| Mean diameter (μm) | 3.4 | 5 |
| Breaking index | 175 | 140 |
| Adhesivity | 100 | 100 |

EXAMPLE 10

An emulsion was made with an aqueous phase obtained by dilution of a concentrated preparation. We thereby simulated here the difficult conditions of preparation of emulsions in units where the possibilities of preparation of emulsifiers in their form of use are limited to simple dilutions of preparations provided in concentrated form. The target emulsion is an emulsion at 60% bitumen turbo-processed under the usual conditions, bitumen 180-220 at 135° for 60%, and aqueous phase at 55° C. at 0.5% of composition $C_1$ prepared both normally by dissolution of the amount required of the cation-active composition in water and acidification, and by dilution of a concentrated composition prepared as in Example 6, and taken up again seven days later.

It can be seen below that the results obtained by the two methods are very equivalent. It goes without saying that the soap deconcentration method is extremely advantageous for the manufacture of bituminous emulsions using mobile units or in installations located on remote sites.

| Emulsifier | $C_1$ | $C_1$ |
|---|---|---|
| Kg/ton of emulsion | 2 | 2 |
| Type of aqueous phase | Standard | Deconcentrated |
| pH value of the emulsion | 2.3 | 2.2 |
| Sieving at 0.60 mm retained % | 0 | 0 |
| Viscosity (mm²s) | 46 | 42 |
| Mean diameter (μm) | 6.0 | 5.9 |
| Breaking index | 140 | 140 |
| Adhesivity | 100 | 100 |

EXAMPLE 11

A method is simulated using an aqueous phase prepared in an installation when it is difficult to heat at a low temperature. Selection was made for fabrication and cold preparation of the emulsifier.

For this purpose a comparison was carried out between an emulsion at 0.2% of the composition, $C_2$, as prepared in the cold state in Example 5 and also used in the cold state, the bitumen remaining the same as previously used at its normal temperature of 135° C., and an emulsion of the same composition prepared under standard conditions.

| Emulsifier | $C_2$ | $C_2$ |
|---|---|---|
| Kg/ton of emulsion | 2 | 2 |
| Temperature of aqueous phase | 19° C. | 55° C. |
| pH value of the emulsion | 2.3 | 2.2 |
| Sieving at 0.60 mm retained % | 0 | 0.15 |
| Viscosity (mm²s) | 46 | 41.5 |
| Mean diameter (μm) | 6.0 | 5.8 |
| Breaking index | 140 | 145 |
| Adhesivity | 100 | 100 |

It can be seen that the operation carried out under these conditions, which are very unusual but very attractive because of their convenience, of low temperature of the aqueous phase, leads to a paving emulsion with a completely acceptable quality.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Compositions of non-flammable, aminated cation-active derivatives which are absolutely liquid at room temperature, and which completely preserve their liquidity when remaining indefinitely exposed to the atmosphere, and which do not lead to the formation of gels, precipitates or deposits when they are kept for prolonged periods at temperatures close to zero degrees centigrade or which do not lead to the formation of gels, precipitates or deposits that persist for long periods of time upon return to room temperature, comprising from about 20 to 80% by weight of an at least ten carbon atom alkyletheramine of the general formula:

in which R is a branched alkyl chain, of the formula:

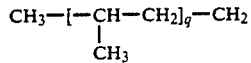

in which q has the value 2 to 5,
n is a whole number equal to 2 or 3
m is a whole number equal to 2 or 3, and
p is a number which can have any value from 0 to 3,
and correspondingly, from about 80 to 20% by weight of oxyalkylated fatty amines or polyamines of the general formula:

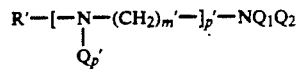

in which R' is a saturated or unsaturated, linear hydrocarbon chain, containing 10 to 22 carbon atoms,
m' is a whole number equal to 2 or 3,
p' is a number which can have value from 0 to 3,
$Q_{p'}$, $Q_1$ and $Q_2$ are each hydrogen, or a hydroxyethyl group-$CH_2$—$CH_2$—OH, or a hydroxyethyloxyethyl group-$CH_2$—$CH_2$—O—$CH_2$—$CH_2$—OH, and can be identical or different, with the sole condition being that they are not all hydrogens.

2. The compositions of claim 1, wherein the alkyletheramines are N-alkyloxypropylpropylenediamines responding to the general formula:

R—O—CH$_2$—CH$_2$—CH$_2$—NH—CH$_2$—CH$_2$—CH$_2$—NH$_2$.

3. The compositions of claim 2, wherein the oxyalkylated fatty polyamines are oxyalkylated alkylpropylene diamines in accordance with the general formula:

R'—NQ$_3$—CH$_2$—CH$_2$—CH$_2$—NQ$_1$Q$_2$ in which $Q_1$, $Q_2$ and $Q_3$ are each hydrogen, a hydroxyethyl group -CH$_2$—CH$_2$—OH, or a hydroxyethyloxyethyl group -CH$_2$—CH$_2$—O—CH$_2$—CH$_2$—OH, and can be identical or different, with the sole condition being that they are not all hydrogens.

4. The compositions of claim 1, consisting essentially of 20 to 80% by weight of N-isotridecyloxypropylpropylenediamine and, correspondingly, 80 to 20% by weight of dioxyethylated oleylpropylenediamine.

5. The method of making bitumen emulsions suitable for use in constructing roadways, comprising admixing a melted bitumen and a dispersant phase and an emulsifying aqueous composition, said aqueous composition containing a cation-active composition comprising from 20 to 80% by weight of at least 10 carbon atoms alkyletheramines of general formula:

R—O—(CH$_2$)$_n$—[—NH—(CH$_2$)$_m$—]$_p$—NH$_2$ in which R is branched alkyl chain, of the formula:

CH$_3$—[—CH(CH$_3$)—CH$_2$]$_q$—CH$_2$ in which q has the value 2 to 5,
n is a whole number equal to 2 or 3,
m is a whole number equal to 2 or 3, and
p is a number which can have a value from 0 to 3,
and from 80 to 20% by weight of oxyalkylated fatty amines or polyamines in accordance with the general formula:

R'—(—N—(CH$_2$)$_{m'}$—)$_{p'}$—NQ$_1$Q$_2$
       |
       Q$_{p'}$ in which R' is a saturated or unsaturated, linear hydrocarbon chain, containing 10 to 22 carbon atoms,
m' is a whole number equal to 2 or 3,
p' is a number which can have an value from 0 to 3,
$Q_{p'}$, $Q_1$ and $Q_2$ are each hydrogen, a hydroxyethyl group -CH$_2$—CH$_2$—OH, or a hydroxyethyloxethyl group -CH$_2$—CH$_2$—O—CH$_2$—CH$_2$—OH, and can be identical or different, with the sole condition being that they are not all hydrogens.

6. The method of claim 5, wherein the alkyl-etheramines are N-alkyloxypropylpropylenediamines of the general formula:

R—O—CH$_2$—CH$_2$—CH$_2$—NH—CH$_2$—CH$_2$—CH$_2$—NH$_2$

7. The method of claim 5, wherein the oxyalkylated fatty polyamines are oxyalkylated alkylpropylene diamines of the general formula:

R'—NQ$_3$—CH$_2$—CH$_2$—CH$_2$—NQ$_1$Q$_2$ in which $Q_1$, $Q_2$ and $Q_3$ are each hydrogen, a hydroxyethyl group -CH$_2$—CH$_2$—OH, or a hydroxyethyloxyethyl group -CH$_2$—CH$_2$—O—CH$_2$—CH$_2$—OH, and can be identical or different, with the sole condition being that they are not all hydrogens.

8. The method of claim 5, 6 or 7, wherein the emulsifying aqueous phase is used at room temperature.

9. The method of claim 5, 6 or 7, wherein the aqueous phase is first prepared at a cation-active aminated composition concentration greater than 100 kg per m3 and then diluted to the concentration for use at the time of employment.

10. The method of claim 5 or 7 wherein the emulsifying aqueous phase comprises a composition consisting of 20 to 80% by weight of N-isotridecyloxypropylpropylenediamine and from 80 to 20% by weight of dioxyethylated oleylpropylenediamine.

* * * * *

UNITED STATES PATENT AND TRADEMARK OFFICE
CERTIFICATE OF CORRECTION

PATENT NO. : 5,098,604
DATED : March 24, 1992
INVENTOR(S) : Brouard, et al

It is certified that error appears in the above-indentified patent and that said Letters Patent is hereby corrected as shown below:

Column 5, line 9, cancel "0/20$\underline{E}$ and substitute therefor -- 0 20$\underline{E}$ --.

Column 12, line 65, before "value" insert "a".

Signed and Sealed this

Thirteenth Day of July, 1993

Attest:

MICHAEL K. KIRK

*Attesting Officer*      *Acting Commissioner of Patents and Trademarks*